United States Patent
Rockrohr et al.

(10) Patent No.: US 8,021,339 B2
(45) Date of Patent: Sep. 20, 2011

(54) SURGICAL PORTAL APPARATUS WITH CENTERING MECHANISM

(75) Inventors: Brian Rockrohr, Waterbury, CT (US); Gregory Fischvogt, Hamden, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 104 days.

(21) Appl. No.: 12/481,808

(22) Filed: Jun. 10, 2009

(65) Prior Publication Data

US 2010/0004600 A1    Jan. 7, 2010

Related U.S. Application Data

(60) Provisional application No. 61/077,300, filed on Jul. 1, 2008.

(51) Int. Cl.
*A61M 5/178* (2006.01)
(52) U.S. Cl. .................. 604/167.04; 604/164.01
(58) Field of Classification Search ............ 604/165.01, 604/159, 167.01–167.04, 256, 164.1; 606/108, 606/167
See application file for complete search history.

(56) References Cited

U.S. PATENT DOCUMENTS

| | | | |
|---|---|---|---|
| 4,795,426 A | 1/1989 | Jones | |
| 4,917,668 A | 4/1990 | Haindl | |
| 4,943,280 A | 7/1990 | Lander | |
| 5,127,909 A | 7/1992 | Shichman | |
| 5,180,373 A | 1/1993 | Green et al. | |
| 5,201,714 A * | 4/1993 | Gentelia et al. | 604/167.04 |
| 5,209,737 A | 5/1993 | Ritchart et al. | |
| 5,342,315 A | 8/1994 | Rowe et al. | |
| 5,360,417 A | 11/1994 | Gravener et al. | |
| 5,389,081 A | 2/1995 | Castro | |
| 5,391,153 A * | 2/1995 | Haber et al. | 604/167.01 |
| 5,397,314 A | 3/1995 | Farley et al. | |
| 5,407,433 A | 4/1995 | Loomas | |
| 5,484,418 A | 1/1996 | Quiachon et al. | |
| 5,492,304 A | 2/1996 | Smith et al. | |
| 5,549,565 A | 8/1996 | Ryan et al. | |
| 5,603,702 A | 2/1997 | Smith et al. | |
| 5,634,908 A | 6/1997 | Loomas | |
| 5,657,963 A | 8/1997 | Hinchliffe et al. | |
| 5,685,854 A | 11/1997 | Green et al. | |
| 5,720,759 A | 2/1998 | Green et al. | |
| 5,722,958 A | 3/1998 | Gravener et al. | |
| 5,727,770 A | 3/1998 | Dennis | |
| 5,752,970 A | 5/1998 | Yoon | |
| 5,820,600 A | 10/1998 | Carlson et al. | |
| 5,895,377 A | 4/1999 | Smith et al. | |
| 5,989,232 A | 11/1999 | Yoon | |
| 6,228,061 B1 | 5/2001 | Flatland et al. | |
| 6,383,160 B1 | 5/2002 | Madsen | |

(Continued)

FOREIGN PATENT DOCUMENTS

EP       1702575       9/2006

(Continued)

*Primary Examiner* — Christopher D Koharski

(57) ABSTRACT

A surgical portal apparatus is provided. The surgical portal apparatus includes a portal member defining a longitudinal axis and having a longitudinal opening therethrough for receiving a surgical object, a seal member positioned along the longitudinal opening for receiving a surgical object in a sealing manner, and a centering mechanism maintained within the portal member, wherein the centering mechanism including a pair of rollers arranged in general diametrical opposed relation, the rollers movable relative to the longitudinal axis from a radial inward position to a radial outward position to permit passage of the surgical object, the rollers being biased toward the radial inward direction to correspondingly bias the surgical object in general alignment with the longitudinal axis.

11 Claims, 5 Drawing Sheets

U.S. PATENT DOCUMENTS

| | | |
|---|---|---|
| 6,458,103 B1 | 10/2002 | Albert et al. |
| 7,025,747 B2 | 4/2006 | Smith |
| 7,063,685 B2 | 6/2006 | Rome |
| 7,105,009 B2 * | 9/2006 | Johnson et al. ............... 606/205 |
| 2002/0072713 A1 | 6/2002 | Almond et al. |
| 2003/0187397 A1 | 10/2003 | Vitali |
| 2004/0064100 A1 | 4/2004 | Smith et al. |
| 2004/0082969 A1 | 4/2004 | Kerr |
| 2004/0167559 A1 | 8/2004 | Taylor et al. |
| 2005/0165281 A1 | 7/2005 | Ravikumar |
| 2006/0020281 A1 | 1/2006 | Smith |
| 2006/0047284 A1 | 3/2006 | Gresham |
| 2008/0091144 A1 | 4/2008 | Moran et al. |

FOREIGN PATENT DOCUMENTS

| | | |
|---|---|---|
| WO | 0152754 | 7/2001 |

* cited by examiner

SURGICAL PORTAL APPARATUS WITH CENTERING MECHANISM

CROSS REFERENCE TO RELATED APPLICATION

The present application claims the benefit of and priority to U.S. Provisional Application Ser. No. 61/077,300 filed on Jul. 1, 2008, the entire contents of which are incorporated herein by reference.

BACKGROUND

1. Technical Field

The present disclosure relates generally to a surgical portal apparatus for accessing the body, and more particularly, relates to a surgical portal apparatus having a centering mechanism for maintaining endoscopic instruments aligned within one or more seals.

2. Background of Related Art

Trocar assemblies and other surgical portal apparatuses are used by surgeons to operate on a patient without having to create large incisions that may become infected and may cause major scarring. Portal apparatuses are known in the art, as are the instruments inserted therethrough for operating within the body cavity. Typically a surgical portal apparatus includes a housing and a cannula. Either or both of the housing and the cannula may include one or more seals for preventing the leakage of insufflation gas through the surgical portal apparatus as an instrument is inserted therethrough and/or in the absence of an instrument. Proper operation of many of these seals may be improved when the instrument being inserted through the surgical portal apparatus are maintained in the center of the seal. Thus, in addition to manipulating the instrument inserted through the surgical portal apparatus to performing a procedure, it may be desirable to maintain the instrument centered within the seal.

Therefore, it would be beneficial to have a surgical portal apparatus that includes a centering mechanism for maintaining an instrument aligned within a seal.

SUMMARY

A surgical portal apparatus is provided. The surgical portal apparatus includes a portal member defining a longitudinal axis and having a longitudinal opening therethrough for receiving a surgical object, a seal member positioned along the longitudinal opening for receiving a surgical object in a sealing manner, and a centering mechanism maintained within the portal member, wherein the centering mechanism including a pair of rollers arranged in general diametrical opposed relation, the rollers movable relative to the longitudinal axis from a radial inward position to a radial outward position to permit passage of the surgical object, the rollers being biased toward the radial inward direction to correspondingly bias the surgical object in general alignment with the longitudinal axis.

The rollers may each include a groove for at least partial reception of the surgical object. Each of the pair of rollers may include an outer tube and an axle. The outer tube may be rotatably received on the axle. The centering mechanism may further include a pair of support members for slidably receiving each of the pair of rollers. The centering mechanism may also include two pairs of springs for biasing the pair of rollers towards one another.

The surgical portal apparatus may further include a second support mechanism. The seal member of the surgical portal apparatus may include at least one of a septum seal, a gel seal, a slit seal valve, an expandable bladder and a zero-closure seal.

BRIEF DESCRIPTION OF THE DRAWINGS

The foregoing summary, as well as the following detailed description will be better understood when read in conjunction with the appended figures. For the purpose of illustrating the present disclosure, various embodiments are shown. It is understood, however, that the present disclosure is not limited to the precise arrangement and instrumentalities shown.

DESCRIPTION OF PREFERRED EMBODIMENTS

Figure 1:
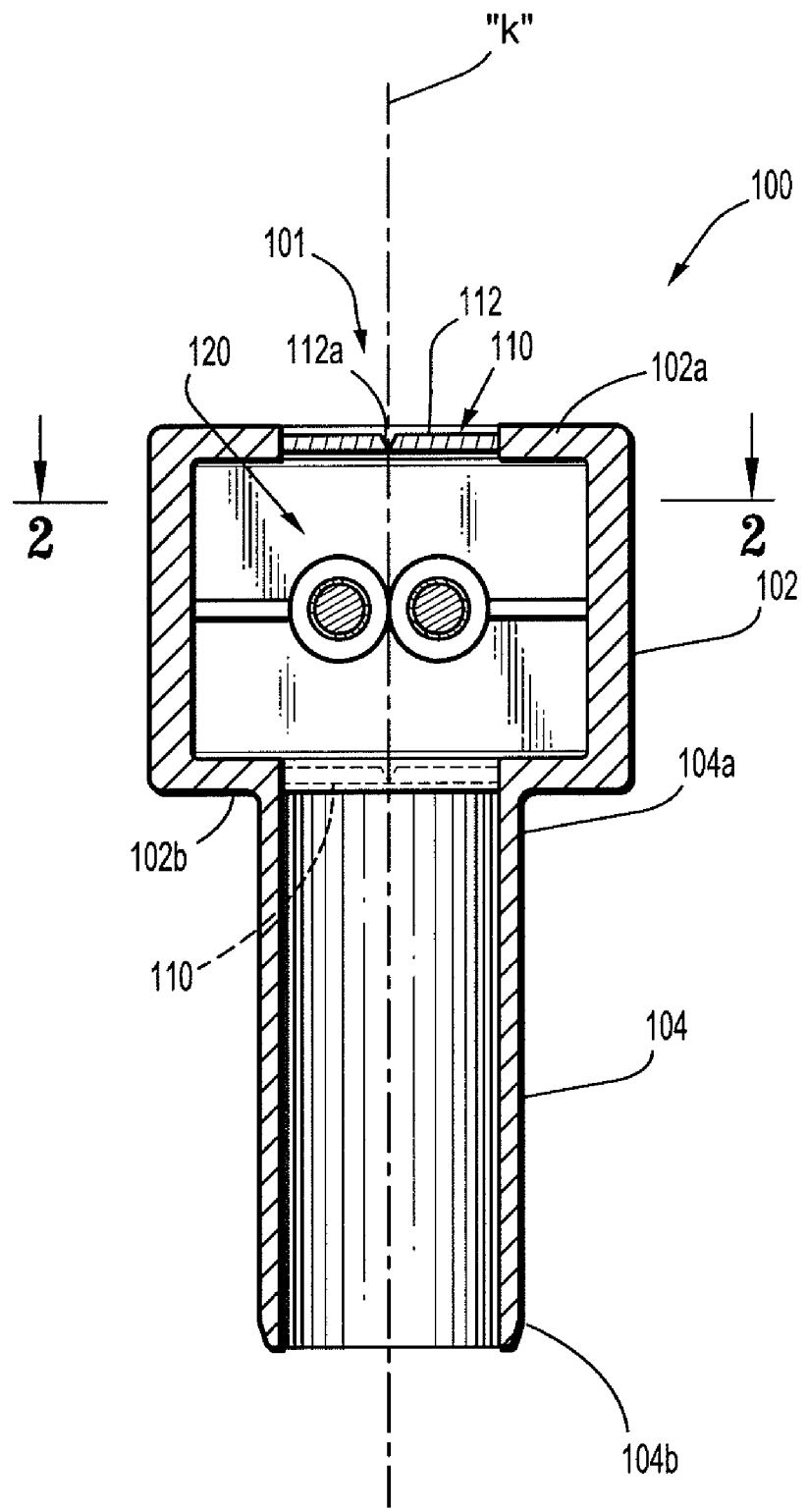
FIG. 1 is a side cross-section view of a surgical portal apparatus according an embodiment of the present disclosure.

Referring now to the drawings wherein like reference numerals illustrate similar components throughout the several views, there is illustrated the surgical portal apparatus 100 in accordance with the principles of the present disclosure. As shown in the drawings and as described throughout the following description, as is traditional when referring to relative positioning on an object, the term "proximal" refers to the end of the apparatus which is closer to the user and the term "distal" refers to the end of the apparatus which is further from the user.

Figure 2:
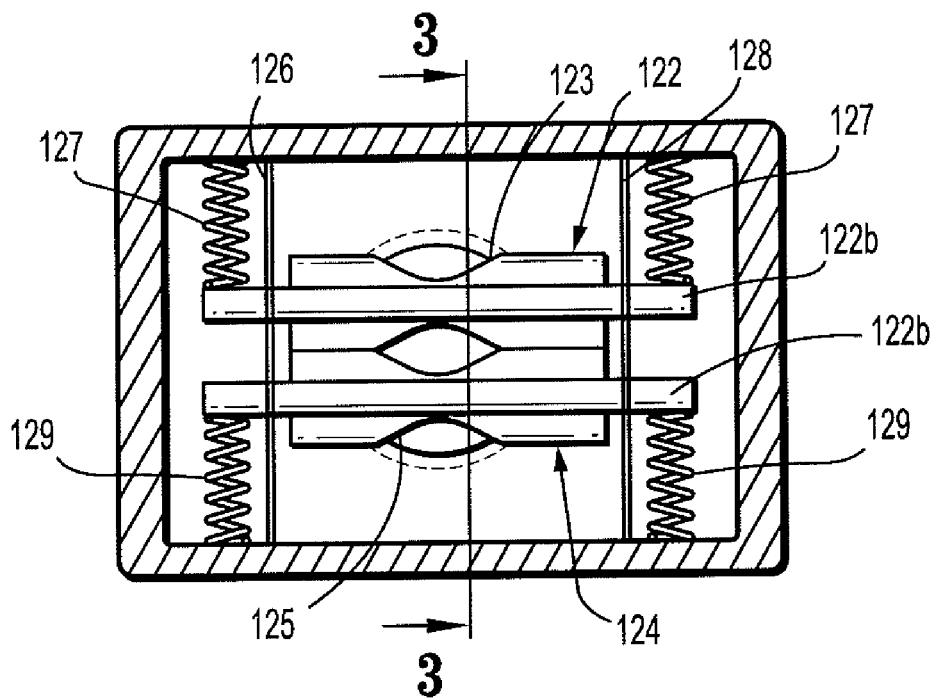
FIG. 2 is an enlarged top cross-section view of the surgical portal apparatus of FIG. 1, taken along line 2-2.

Referring initially to FIGS. 1 and 2, surgical portal apparatus 100 is shown in the form of a cannula assembly. Surgical portal apparatus 100 includes a housing or portal member 102 and a cannula sleeve 104 extending distally from housing 102 and defines a longitudinal axis "k". Surgical portal apparatus 100 may be configured for use with any known endoscopic or laparoscopic instrument. Cannula sleeve 104 is configured to be inserted through the skin into a body cavity with the aid of an obturator (not shown). Cannula sleeve 104 may instead include a blade or piercing tip for penetrating through the skin and into a body cavity. Cannula sleeve 104 may be integral formed with housing 102. Alternatively, cannula sleeve 104 may be configured for selectable engagement with housing 102.

Cannula sleeve 104 forms a substantially tubular member having proximal and distal ends 104a, 104b. Cannula sleeve 104 may be composed of plastic, metal, polymers or the like. Cannula 104 may be disposable, or in the alternative, reusable. Cannula sleeve 104 may be solid, or alternatively, cannula sleeve 104 may be flexible. Distal end 104b of cannula sleeve 104 may be open. Distal end 104b may instead be configured to include one or more seal members (not shown). Cannula sleeve 104 may be of any configuration and of any length or diameter. Thus, it is appreciated that the embodiments of the present disclosure are not limited by the configuration of cannula sleeve 104 and may be configured for use with any conceivable cannula assembly configuration.

Figure 3:
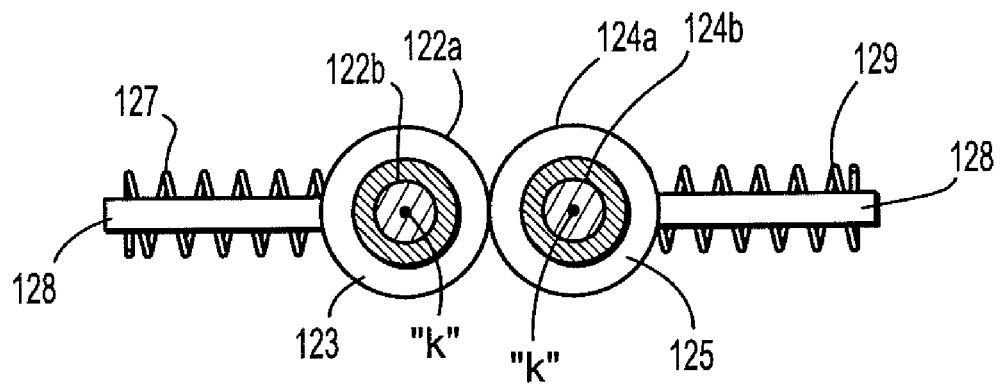
FIG. 3 is a side cross-sectional view illustrating the centering mechanism of the surgical portal apparatus of FIG. 2, taken along line 3-3.
Figure 4:
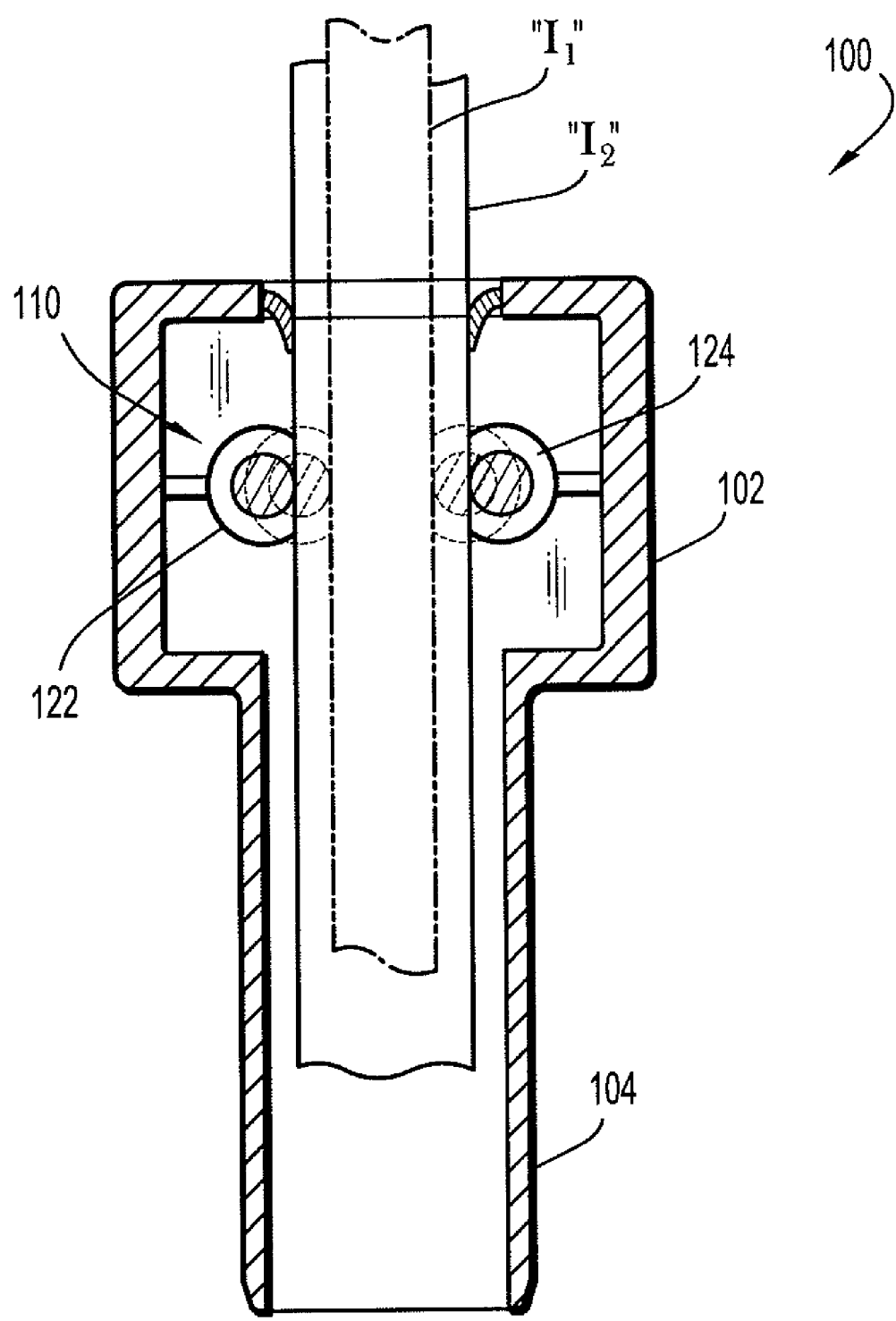
FIG. 4 is a side cross-sectional view of the surgical portal apparatus of FIGS. 1-3 illustrating endoscopic instruments of various sizes inserted therethrough.
Figure 5:
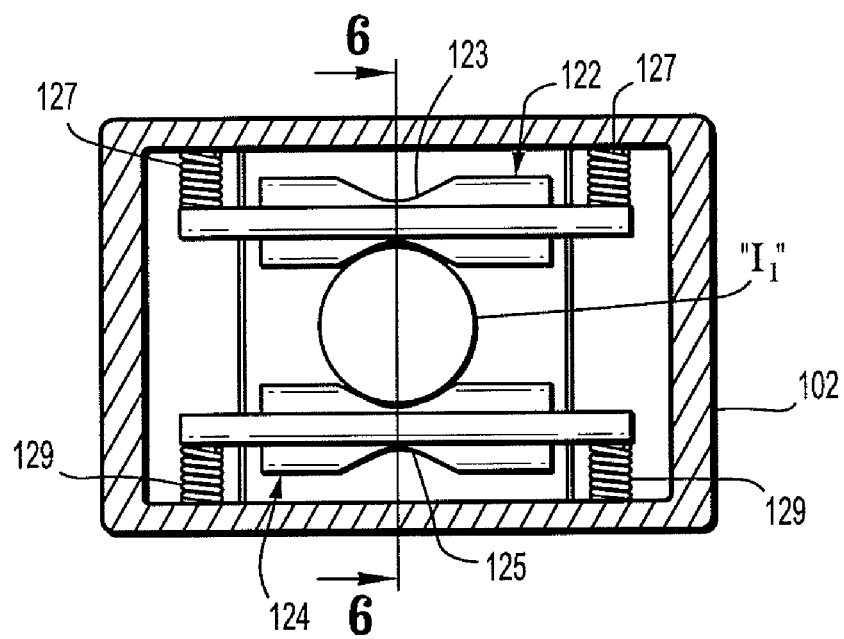
FIG. 5 is an enlarged top cross-sectional view of the surgical portal apparatus of FIG. 4, taken along line 5-5.
Figure 6:
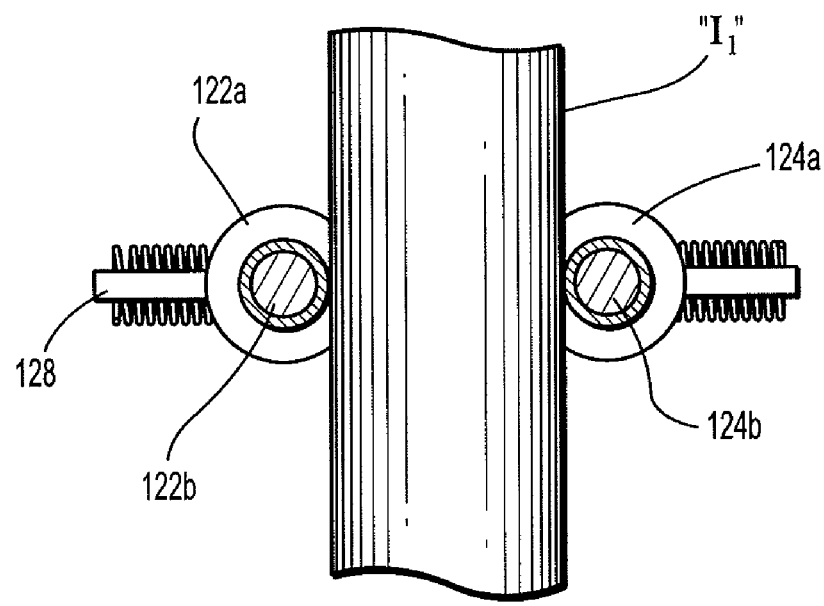
FIG. 6 is a side cross-sectional view illustrating the centering mechanism of the surgical portal apparatus of FIG. 5, taken along line 6-6.
Figure 7:
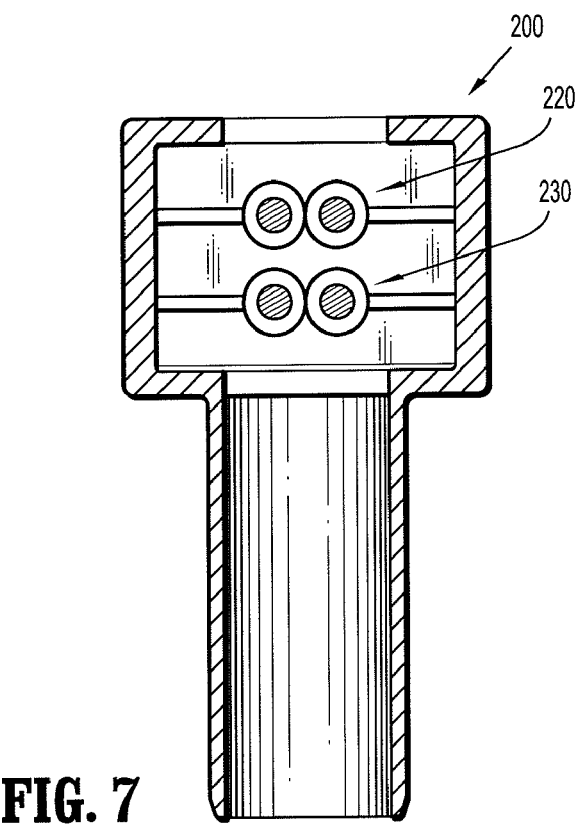
FIG. 7 is a side cross-sectional view of a surgical portal apparatus according to an alternate embodiment of the present disclosure; and, FIG. 8 is a side cross-section view of the surgical portal apparatus of FIG. 7, including an instrument inserted therethrough.

Referring now to FIGS. 3-5, housing 102 of surgical portal apparatus 100 defines a passageway 101 therethrough configured for receiving endoscopic instruments of various diameters. Housing 102 includes a seal member 110 and a centering mechanism 120.

Seal member 110 extends about an inner surface of housing 102, preferably about a proximal end 102a of housing 102. However, it is envisioned that first seal member 110 may be disposed anywhere along the length of passageway 101. Seal member 110 may comprise any known seal configurations, including a septum seal, gel seal, slit seal valve, expandable bladder, zero-closure seal or the like. Seal member 110 may include one or more seal surfaces 112. Seal member 110 is configured for sealably receiving an endoscopic instruments "$I_1$", "$I_2$" having various diameters. Seal surface 112 may be formed of rubber, plastic, polymer or the like. An instrument contacting end 112a of seal surface 112 may be tapered to facilitated sealing about endoscopic instrument "$I_1$", "$I_2$" (FIG. 4).

Still referring to FIGS. 3-5, centering mechanism 120 includes first and second rollers 122, 124 mounted to first and second support members 126, 128. Each of first and second rollers 122, 124 includes an outer tube 122a, 124a and an axle 122b, 124b, respectively. Outer tubes 122a, 124a are configured to rotate freely on axles 122b, 124b, respectively, about axes of rotation "k". In an alternative embodiment, outer tubes 122a, 124a may be secured to or integrally formed with axles 122b, 124b. Outer tubes 122a, 124a may be constructed of plastic, polymer or other like material. Outer tubes 122a, 124a include instrument engaging grooves 123, 125, respectively. Grooves 123, 125 may be configured, as shown, in a wedge formation, or may otherwise be formed to engage various instruments. Grooves 123, 125 may be coated with rubber or other suitable material (not shown) to protect instruments from damage as they are inserted through housing 102. Axles 122b, 124b each slidable engage support mounts 126, 128. Support mounts 126, 128 extend across housing 102 and permit lateral movement of rollers 122, 124. Support mounts 126, 128 may serve as track mounts defining longitudinal rails or grooves for receiving axles 122b, 124b. Axels 122b, 124b of rollers 122, 124 are engaged by a first and second pair of springs 127, 129, respectively. Springs 127, 129 bias rollers 122, 124, respectively, towards one another and radially inwardly relative to longitudinal axis "k" of portal apparatus 100. It is envisioned that springs 127, 129 may be replaced by hydraulic pistons, pneumatic cylinder or other suitable mechanism or material. Springs 127, 129 may be received within longitudinal rails defined by support mounts 126, 128.

With reference now to FIGS. 1-7, surgical portal apparatus 100 will be described as relates to the operation of seal members 110 and centering mechanism 120. Referring initially to FIGS. 1-3, in a first or initial condition, rollers 122, 124 of centering mechanism 120 are biased radially inwardly towards one another within housing 102. Grooves 123, 125 formed in rollers 122, 124, respectively, may form an opening which permits the passage of an endoscopic instrument having a small diameter, without engaging centering mechanism 120. As discussed above, seal member 110 may be positioned anywhere along passage 101, including in proximal or distal ends 102a, 102b of housing 102 and along cannula 104. Surgical portal apparatus 100 may be inserted into the body cavity of a patient (not shown) in any conventional manner.

Turning now to FIGS. 4-7, once received within the body cavity (not shown), surgical portal apparatus 100 may receive in a sealing manner, instruments "$I_1$", "$I_2$" of differing diameter. As shown, instruments "$I_1$", "$I_2$" are initially received through seal member 110 formed in proximal end 102a of housing 102. Engagement of the distal end of instrument "$I_1$", "$I_2$" within grooves 123, 125 of outer tube 122a, 124a, respectively, causes outer tubes 122a, 124a to rotate about axles 122b, 124b as first and second rollers 122, 124 are moved away from one another in order to accommodate the passage of instrument "$I_1$", "$I_2$" therethrough. Springs 127, 128 bias respective rollers 122, 124 inward towards instrument "$I_1$", "$I_2$" thereby maintaining instruments "$I_1$", "$I_2$" within grooves 123, 125. In this manner, centering mechanism 120 is configured to maintain instruments "$I_1$", "$I_2$" of differing diameters centered within housing 102, and thereby centered within seal member 110. Removal of instrument "$I_1$", "$I_2$" from between rollers 122, 124 results in rollers 122, 124 returning to an initial position (FIGS. 1-3).

Figure 8:
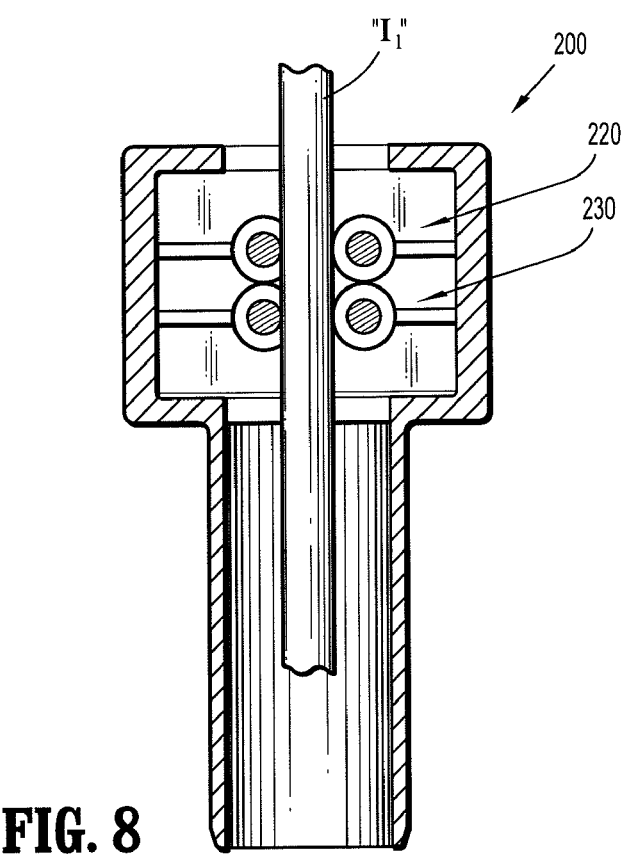

With reference now to FIGS. 8 and 9, a surgical portal apparatus according to an alternate embodiment of the present disclosure is shown generally as surgical portal apparatus 200. Surgical portal apparatus 200 is substantially similar to surgical portal apparatus 100, and will only be described as relates to the differences therebetween. Surgical portal apparatus 200 includes first and second centering mechanism 220, 230. Each of first and second centering mechanisms 220, 230 are substantially similar to centering mechanism 120 described hereinabove. First and second centering mechanism 220, 230 may be configured to operate together to more securely maintain an endoscopic instrument "$I_1$" therethrough, e.g. in a general alignment with the longitudinal axis of surgical portal apparatus 100.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims append hereto.

What is claimed is:

1. A surgical portal apparatus, which comprises:
   a portal member defining a longitudinal axis and having a longitudinal opening therethrough for receiving a surgical object;
   a seal member positioned along the longitudinal opening for receiving a surgical object in a sealing manner; and
   a centering mechanism maintained within the portal member, wherein the centering mechanism includes a pair of rollers arranged in general diametrical opposed relation, each roller adapted to rotate about an axis of rotation, the rollers movable relative to the longitudinal axis from a radial inward position to a radial outward position along a common plane to permit passage of the surgical object, each of the rollers being biased toward the radial inward direction by a pair of springs to correspondingly bias the surgical object in general alignment with the longitudinal axis.

2. The surgical portal apparatus according to claim 1 wherein the rollers each include a groove for at least partial reception of the surgical object.

3. The surgical portal apparatus according to claim 2 wherein the centering mechanism further includes a pair of support members for slidably receiving each of the pair of rollers.

4. The surgical portal apparatus according to claim 2 wherein each groove extend completely about each roller.

5. The surgical portal apparatus according to claim 1 wherein each of the pair of rollers includes an outer tube and an axle.

6. The surgical portal apparatus according to claim 5 wherein the outer tube is rotatably received on the axle.

7. The surgical portal apparatus according to claim 1 further including a second support mechanism.

8. The surgical portal apparatus according to claim 1 wherein the seal member includes at least one of a septum seal, a gel seal, a slit seal valve, an expandable bladder and a zero-closure seal.

9. The surgical portal apparatus according to claim 1 wherein each of the rollers operably engage support mounts for permitting movement between the radial inward position and the radial outward position.

10. The surgical portal apparatus according to claim 9 wherein the support mounts include a pair of rails.

11. The surgical portal apparatus according to claim 10 wherein each of the rollers slide along the pair of rails.

* * * * *